United States Patent [19]

Hughes

[11] Patent Number: 5,766,008
[45] Date of Patent: Jun. 16, 1998

[54] INTRACORONAL BRISTLE BRUSH

[76] Inventor: Michael F. Hughes, 1205 Jacaranda Blvd., Venice, Fla. 34292

[21] Appl. No.: 688,665

[22] Filed: Jul. 29, 1996

[51] Int. Cl.⁶ .................................................. A61C 3/00
[52] U.S. Cl. ...................... 433/165; 15/191.1; 15/167.1; 15/179
[58] Field of Search ...................... 433/125, 142, 433/165, 166, 131, 141, 103; 15/192, 193, 180, 28, 191.1, 167.1, 179

[56] References Cited

U.S. PATENT DOCUMENTS

| | | | |
|---|---|---|---|
| 361,806 | 4/1887 | Ballard | 433/166 X |
| 2,160,731 | 5/1939 | Haeberlin | 15/167.1 |
| 2,449,158 | 9/1948 | Benyak | 15/179 X |
| 5,000,684 | 3/1991 | Odrich | 433/125 |
| 5,001,801 | 3/1991 | Jarvis et al. | |
| 5,150,495 | 9/1992 | Discko, Jr. et al. | 15/167.1 |

OTHER PUBLICATIONS

Promotional Brochure for Benda Brush, Centrix Incorporated, undated.

*Primary Examiner*—Jeffrey A. Smith
*Attorney, Agent, or Firm*—Stein, Pendorf & Van Der Wall

[57] ABSTRACT

An intracoronal bristle brush for preparing a tooth cavum comprising a plurality of bristles and a dental bit having a first end being a shank adapted to be received by a dentist's handpiece and a second end for receiving the plurality of bristles. The plurality of bristles emanate outwardly in a uniform manner from an axial hole within the second end. The diameter of the intracoronal bristle brush is substantially uniform along its entire length such that the bristles of the brush may penetrate into an interior surface of a tooth cavum.

2 Claims, 2 Drawing Sheets

U.S. Patent  Jun. 16, 1998  Sheet 1 of 2  5,766,008
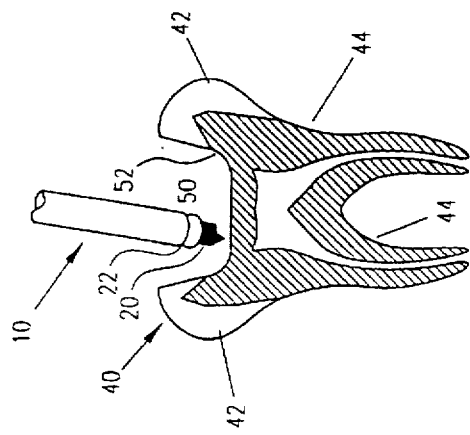
FIG. 4
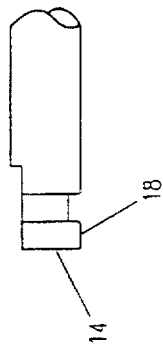
FIG. 3
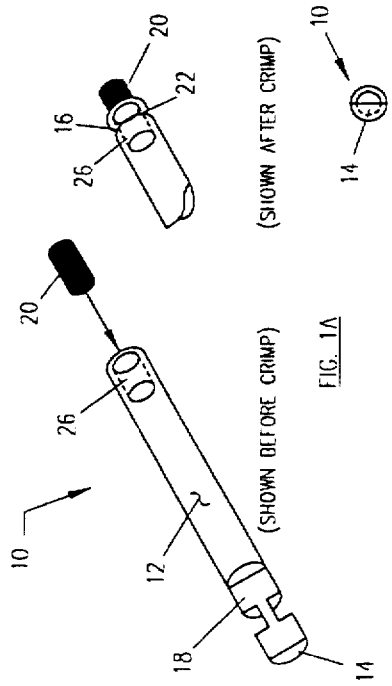
FIG. 1A (SHOWN BEFORE CRIMP)
FIG. 1B (SHOWN AFTER CRIMP)
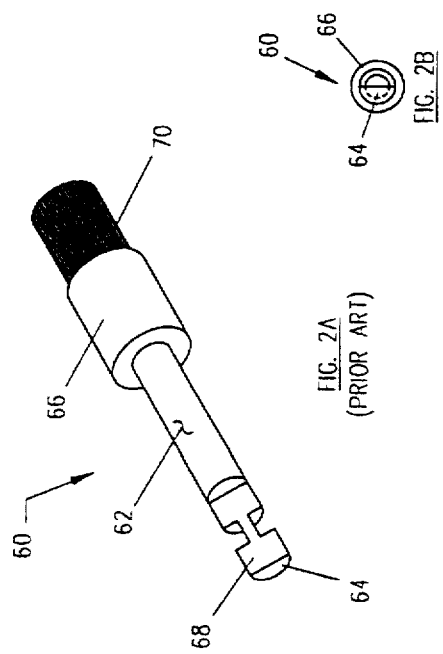
FIG. 2A (PRIOR ART)
FIG. 2B

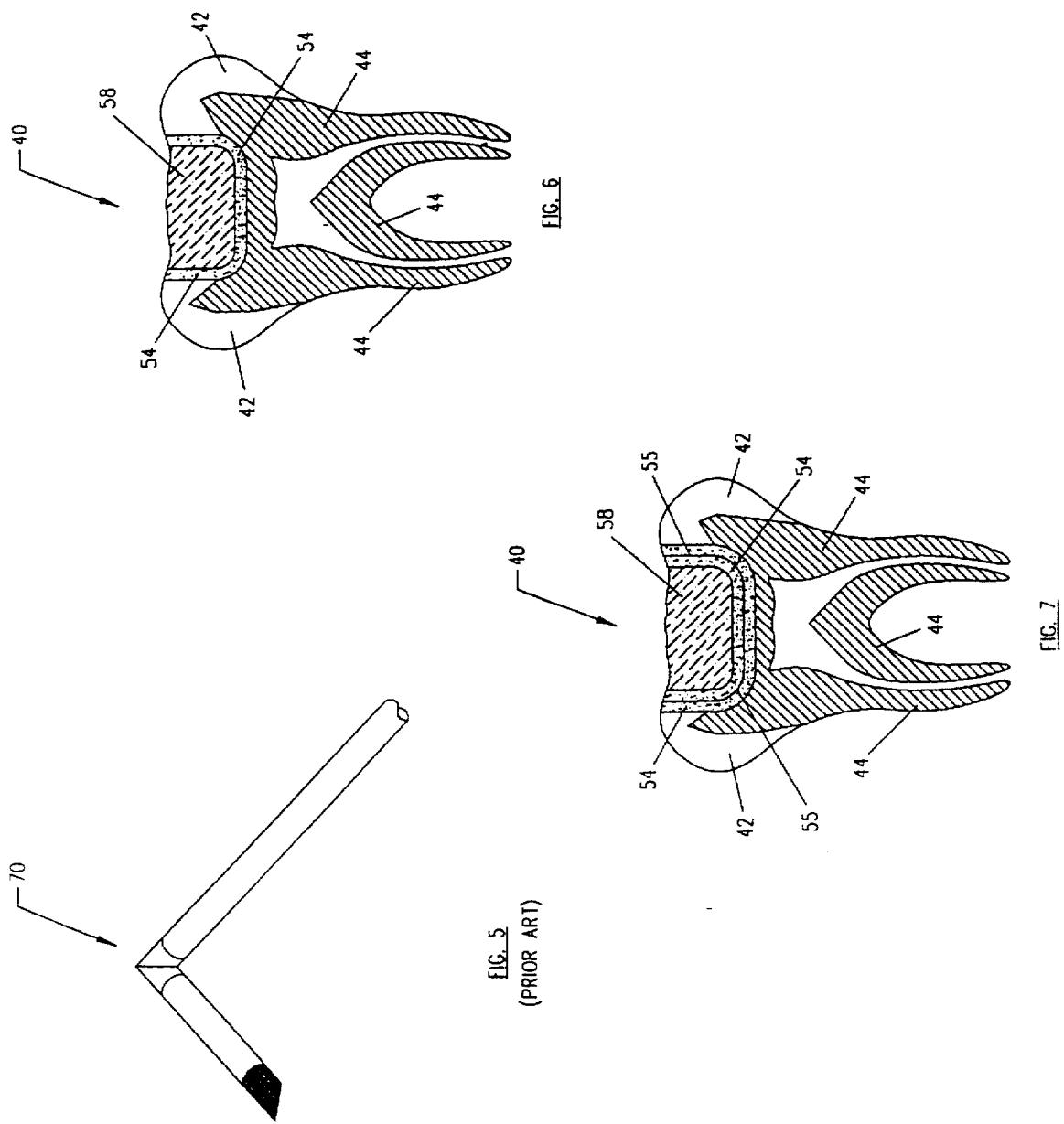

INTRACORONAL BRISTLE BRUSH

BACKGROUND OF THE INVENTION

1. Field of the Invention

The present invention relates to brushes adapted to a dental handpiece. This invention more particularly pertains to dental brushes for handpieces capable of cleaning within a cavum of a tooth.

2. Description of the Background Art

Presently, the only commercially available dental brushes for handpieces merely comprise of a shank portion on one end and a bristle portion placed upon the other end. This type of dental brush has a larger diameter on the end with the bristles such that the bristles of the brush may not be fitted into a cavum of a tooth.

This known brush is used during a typical teeth cleaning performed by a dentist or a hygienist. This cleaning is typically called a prohylaxis cleaning. Subsequently, the bristle brush used during this procedure has become known as a prophy brush. As a result of the desire to secure numerous bristles to the brush, the bristle end of the prophy brush is substantially larger in diameter than the shank diameter that is fitted within the handpiece. This limits the access to the inner surface of a tooth cavum with a prophy brush that would be fitted to a handpiece. Consequently, the prophy brush is limited in use during a prophylaxis cleaning to merely cleaning the outside surface of a tooth.

While these prophy brushes work well for cleaning the outside of a tooth in preparation of filling a cavity or some other dental technique, it was quickly learned that a dental brush that was capable of fitting within the cavum of a tooth was necessary. A typical example of this brush is illustrated in FIG. 5 which is designed solely for applying liquids as in a paint brush. This brush is flexible and may be utilized to access the inner surface of a tooth cavum. However, this device is not adaptable to the dentist's handpiece. This device is merely designed for use in a dentist's hand and is only for applying adhesive to a tooth for retaining fillings. The device, illustrated in FIG. 5, is not designed for cleaning the surfaces of a tooth.

In response to the realized inadequacies of these earlier brushes, it became clear that there is a need for a simple bristle brush that may be used by a dentist with the aid of a handpiece. This device must provide for intricate access to the inner cavum surface of a tooth for cleaning so that adhesive may properly bond. In as much as the art consists of various types of dental brushes, it can be appreciated that there is a continuing need for and interest in improvements to dental brushes, and in this respect, the present invention addresses these needs and interests.

Therefore, the principal object of this invention is to provide an improvement which overcomes the aforementioned inadequacies of the prior art devices and provides an improvement which is a significant contribution to the advancement of the dental brush art.

Another object of this invention is to provide a new and improved dental brush which has all the advantages and none of the disadvantages of the earlier brushes.

Still another objective of the present invention is to provide an easily manufactured dental brush.

Yet another objective is to provide a dental brush that accesses the inner surface of a tooth cavum.

Still a further objective of the present invention is to provide a dental brush adaptable for use with a handpiece.

Yet a further objective is to provide a means to improve the bond between the adhesive applied to the surfaces within a prepared tooth and the filling material by removing the smear layer of debris.

An additional objective is to provide a method by which a cavity in a tooth may be more effectively repaired.

Another objective is to improve the patient's comfort during the tooth restoration process.

Even yet another objective is to improve the reliability of the repaired tooth once it has been repaired.

Still yet another objective of the present invention is a more rapid completion of the tooth repair process.

A further objective is to provide a repaired tooth comprising a tooth; a cavum having an interior surface formed in the tooth, the cavum having been cleaned with an intracoronal bristle brush impregnated with a cleaning substance, the intracoronal bristle brush comprising a plurality of bristles having a brush diameter; a dental bit with a central axis along the length and having a substantially uniform diameter thereof, the dental bit having first and second ends, and the first end being a shank adapted to be received by a handpiece, the second end having an axial hole formed therein for receiving the plurality of bristles such that the bristles emanate outwardly in a uniform manner, and the diameter of the dental bit and the brush diameter remaining substantially uniform along the length of the intracoronal bristle brush; an adhesive deposited within the cavum after cleaning, the adhesive being brushed to the interior surface of the cavum; and a filling material generally shaped to fill the cavum, the filling material bonded to the tooth.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a more comprehensive understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

The present invention is defined by the appended claims with the specific embodiment shown in the attached drawings. This invention satisfies the need for a handpiece brush that may be easily inserted into the cavum while preparing a tooth. For the purpose of summarizing this invention, this invention comprises a plurality of bristles where the combined bristles have a brush diameter. The bristles are attached to a dental bit which has two ends. The dental bit has a central axis along its length. The first end is a typical shank capable of being received by a dentist's handpiece. The second end is for attaching the bristles which emanate outwardly in a uniform manner. The second end of the dental bit has an axial hole for receiving the plurality of bristles. The bristles and the dental bit are of substantially the same diameter such that the diameter of the dental brush remains substantially uniform along its length.

This invention further comprises a tooth with a repaired cavum. The tooth had a cavity. When the decay creating this cavity is removed, a cavum with an interior surface is formed inside. Thus, removing the decay creates a dental cavum defined by the interior surface which when filled will constitute a reconstructed tooth.

In some instances, a dentin primer is first painted on to the interior surface of the cavum to aid in bonding a filling material. An adhesive is then brushed to the interior surface of the cavum within the exposed tooth. Finally, a filling material is placed upon the cavum and packed down within the cavum. The filling material is shaped to conform to the shape of the desired tooth. Typically, fillings were of silver. Presently, fillings are of a composite in the form of a paste which are typically cured by auto-polymerization or light polymerization.

The present invention further comprises a method for filling a cavum in a tooth. The first step is to prepare the tooth having the cavity. The tooth is prepared by removing the decay which then forms a cavum in the tooth. Next, this preparation consists of cleaning the tooth with an intracoronal bristle brush on a handpiece. The cleaning substance typically used is pumice. The cleaning substance is impregnated upon the bristle brush.

Next, an etching gel is used to rough up the dentin and enamel surfaces of the tooth so that microretentive surface characteristics are created. The etching gel typically consists of phosphoric acid. As a result of this etching technique, the teeth and mouth of the patient must be thoroughly rinsed to remove excess etching gel. Any further excess materials may be suctioned out. In some instances, a dentin primer may be placed within the cavum of the tooth to aid in bonding the filling material. Then, the mouth is dried with air to remove excess moisture.

The bonding adhesive is then applied to the exposed dentin and enamel of the tooth to form micromechanical and chemical bonds with a brush. This brush is different from the intracoronal bristle brush in that the intracoronal bristle brush is used to clean the cavum by removing the smear layer of debris before acid etching. Some cure time may be necessary for the adhesive prior to bonding with a filling material.

Finally, filling material is positioned upon the tooth being repaired and packed within the cavum. It may be necessary for the filling material to be shaped so that the material conforms to the desired specifications for the repaired tooth. Also, some cure time may be necessary for the filling material to set.

An important feature of the present invention is that the intracoronal bristle brush is of substantially a uniform diameter which may be used in a handpiece as well as inside a tooth cavum.

Therefore, it can be readily seen that the present invention provides a means to access the interior surface of a tooth cavum for cleaning to facilitate the bonding process. Thus, a dental brush for cleaning inside a tooth cavum with a handpiece provides capabilities that would be appreciated.

The foregoing has outlined rather broadly, the more pertinent and important features of the present invention. The detailed description of the invention that follows is offered so that the present contribution to the art can be more fully appreciated. Additional features of the invention will be described hereinafter. It should be appreciated by those skilled in the art that the conception and the disclosed specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more succinct understanding of the nature and objects of the invention, reference should be directed to the following detailed description taken in connection with the accompanying drawings in which:

FIG. 1A is a perspective view of the intracoronal bristle brush for a dental handpiece having a central axis according to the preferred embodiment of the present invention.

FIG. 1B is a left end view of the intracoronal bristle brush for a dental handpiece according to the preferred embodiment.

FIG. 2A is a perspective view of the prior art dental brush for a dental handpiece.

FIG. 2B is a left end view of the prior art dental brush for a dental handpiece.

FIG. 3 is a front view, rotated 90 degrees and partly in section, of the shank portion of the intracoronal bristle brush as shown in FIG. 1.

FIG. 4 is a sectional view of the inside surface of a tooth being cleaned with the intracoronal bristle brush.

FIG. 5 is a perspective view, partial section, of a prior art dental brush for applying adhesive without a handpiece.

FIG. 6 is a cross-sectional view of a repaired tooth with adhesive and a filling material.

FIG. 7 is a cross-sectional view of a repaired tooth with dentin primer, adhesive and a filling material.

Similar reference characters refer to similar parts throughout the several views of the drawings.

DETAILED DESCRIPTION OF THE PREFERRED EMBODIMENT

With reference to the drawings, and in particular to FIG. 1A, a new and improved intracoronal bristle brush embodying the principles and concepts of the present invention and generally designated by the reference numeral 10 will be described. As shown in FIG. 1A, the intracoronal bristle brush 10 comprises a dental bit 12 and a plurality of bristles 20. The dental bit 12 has a first end 14 and a second end 16. The first end 14 is a shank 18 adapted to be received by a dentist's handpiece. The second end 16 has an axial hole 26 for receiving the plurality of bristles 20. FIG. 3 illustrates the typical shank 18 adapted for use in a dentist's handpiece. In the preferred embodiment as shown in FIG. 1A, the plurality of bristles 20 emanate outwardly in a uniform manner and are secured into the axial hole 26 of the second end 16 by the means of a crimp 22 which deforms the axial hole 26 to rigidly retain the plurality of bristles 20 within.

The prior art prophy brush 60 as shown in FIG. 2A comprises a dental bit 62 and a plurality of bristles 70. The prophy brush 60 has a first end 64 and a second end 66. The first end 64 is a shank 68 adapted to be received by a dentist's handpiece. The plurality of bristles 70 are secured onto the second end 66. As shown in FIGS. 2A and 2B, it may be seen that the structure of the means for securing the plurality of bristles 70 and the second end 66 of the dental bit 62 prevents the bristle brush 60 from being utilized in the cavum 50 of the tooth 40 and is, therefore, distinguishable from the prior art.

As shown in FIGS. 1A and 1B, the intracoronal bristle brush 10 of the invention is of a substantially uniform structure and diameter throughout. The uniformity in structure throughout the intracoronal bristle brush 10 facilitates the cleaning the enamel 42 and dentin 44 of the interior surface 52 for a tooth 40. FIG. 4 illustrates the ease of positioning the intracoronal bristle brush 10 within the cavum 50 of a tooth 40. FIG. 4 also illustrates the intracoronal bristle brush 10 in contact with the interior surface 52 of the tooth 40. The relative ease with which the present invention of the intracoronal bristle brush 10, adapted for use with a handpiece, may access the interior surface 52 of a tooth 40 may be appreciated.

FIG. 5 illustrates a prior art bristle brush 70 which is not adaptable for use in a dentist's handpiece.

In addition, as illustrated in FIG. 6, the invention comprises a tooth 40 having had the interior surface 52 cleaned with the present invention of the intracoronal bristle brush 10. Also, in some instances, the interior surface 52 of the tooth 40 has dentin primer 55 placed upon the interior surface 52 to aid some types of adhesive 54 in retaining the filling material 58 as shown in FIG. 7. The tooth 40 has had adhesive 54 applied on to the interior surface 52 after priming. The adhesive 54 then bonds the filling material 58 into the tooth 40.

The present invention, in addition to the repaired tooth 40 and the intracoronal bristle brush 10, also includes the method of repairing the tooth 40. The method includes the step of removing tooth decay to form said cavum 50 having an interior surface 52. The interior surface 52 is then prepared by cleaning with the intracoronal bristle brush 10 of the present invention impregnated with a cleaning substance. The method then includes the step of etching the tooth 40 with etching gel consisting of phosphoric acid so that microretentive surface characteristics are produced. The next step is to thoroughly rinse out the excess etching gel. After rinsing, dentin primer 55 is sometimes applied onto the interior surface 52 of the cavum 50 when using some types of adhesive 54. Next, air is applied to remove excess moisture. The method then includes the step of applying adhesive 54 to the interior surface 52 of the cavum 50. Then, a filling material 58 is packed into the tooth 40.

The invention further comprises a method wherein the step of preparing the tooth 40 with the intracoronal bristle brush 10 includes cleaning the tooth 40 with pumice.

In addition, the invention further comprises a method wherein the step of applying adhesive 54 includes curing the adhesive 54.

Also, the invention further comprises a method wherein the step of packing the filling material 58 includes shaping the filling material 58 to form the tooth 40.

The invention further comprises a method wherein the step of rinsing includes suctioning out moisture prior to applying adhesive 54.

Also, the invention further comprises a method wherein the step of packing the filling material 58 includes curing the filling material 58.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. An intracoronal bristle brush for use with a dental handpiece for preparing a tooth cavum comprising, in combination:

a plurality of bristles forming a brush diameter;

a dental bit with a central axis along the length and having a substantially uniform diameter thereof, said dental bit also having first and second ends, said first end being a shank adapted to be received by the handpiece, said second end having an axial hole formed therein for receiving said plurality of bristles such that said plurality of bristles emanate outwardly in a uniform manner, said plurality of bristles disposed in said axial hole, and said diameter of said dental bit and said brush diameter remaining substantially uniform along the length of said intracoronal bristle brush.

2. The intracoronal bristle brush as claimed in claim 1, wherein said dental bit further comprises a mechanical crimp such that said axial hole is deformed in order to rigidly retain said plurality of bristles therein.

\* \* \* \* \*